United States Patent

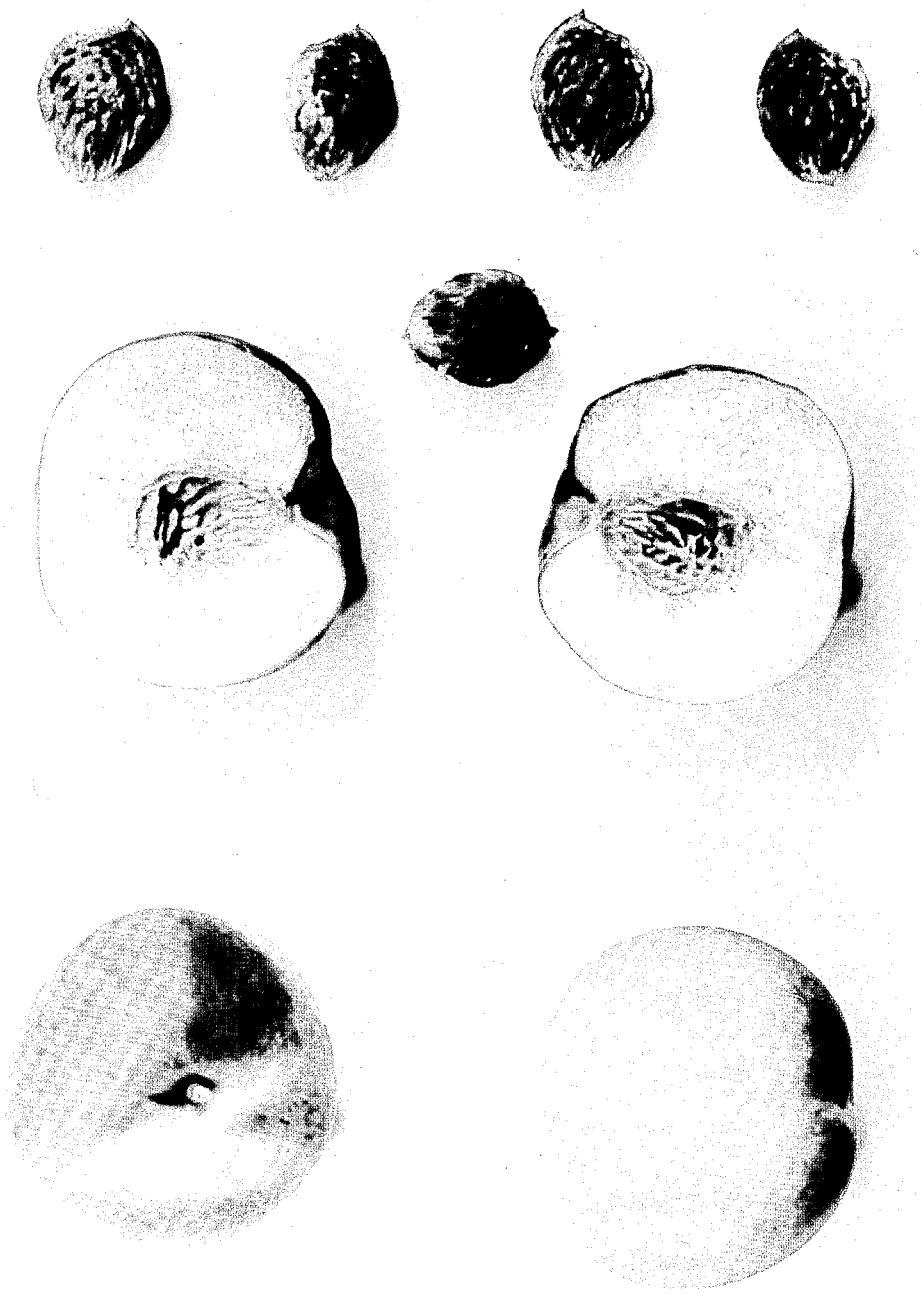

Plant Pat. 3,934

Patented July 6, 1976

3,934

PEACH TREE

Charles Preuss, 8690 N. Minnewawa Ave., Clovis, Calif. 93612

Filed June 27, 1975, Ser. No. 590,825

Int. Cl.[2] A01H 5/03

U.S. Cl. Plt.—43 1 Claim

ABSTRACT OF THE DISCLOSURE

A peach tree resulting from a sport of a Preuss Suncrest of U.S. Plant Pat. No. 2,797 which it most nearly resembles in bearing large free-stone, darkly red-skinned, yellow-fleshed peaches but from which it is distinguished in that its fruit are more nearly spherical, somewhat lighter and brighter red, firmer and ripen approximately six days earlier.

ORIGIN

The peach tree of the present invention occurred as a limb sport in an orchard of Preuss Suncrest peach trees (U.S. Plant Pat. No. 2,797) at 8690 N. Minnewawa, near the city of Clovis, county of Fresno and State of California owned by the applicant.

DISCOVERY

The new variety was discovered in the Preuss Suncrest orchard by the applicant when it attracted his attention as bearing fruit which were more nearly spherical, a somewhat lighter and brighter red and ripened approximately six days earlier than the Preuss Suncrest.

ASEXUAL REPRODUCTION

After observing the new variety, the applicant budded selected buds from it into host trees in his orchard identified above. The buds grew successfully and were carefully observed. They were found to maintain the characteristics of the originally discovered sport in all observable respects including the distinctions over the Preuss Suncrest noted above.

SUMMARY

The present variety of peach tree generally possesses the attributes of the Preuss Suncrest peach trees as to vigor of growth, large size, regular and heavy bearing and in the production of large, free-stone, red and yellow-skinned, firmly textured, yellow-fleshed peaches but is distinguished from the Preuss Suncrest in the red coloration of the fruit being somewhat lighter and brighter but less extensively dominant over the yellow, firmer, more nearly spherical and ripening six days earlier. The latter distingushing characteristic is particularly significant to the commercialization of the new variety, it being well known in the fresh fruit industry that a difference in ripening time of only a few days can make the difference between an economically successful year or an actual loss. Usually the earlier ripening of fruit of given characteristics is a distinct pricing advantage.

The new variety blooms in the latter part of March at about the same time as the Fay Elberta (unpatented) and the Preuss Suncrest. The blossoms are self pollinating, of large size and pale to moderate pink (2.5R 9/3–5R 8/5) with some darkening to strong pink (2.5R 7/8).

The fruit usually ripens during the third quarter of July about six days earlier than the Preuss Suncrest and the Merrill 49er (unpatented).

BRIEF DESCRIPTION OF THE DRAWING

The accompanying drawing is a color photograph of:

1. two peaches of the present variety, one being viewed from the stem and the other from the side in the sature plane;
2. two peach halves severed on the suture plane to show flesh coloration; and
3. a number of characteristic stones viewed from various positions to illustrate their characteristics.

DESCRIPTION OF THE NEW VARIETY

Referring in greater detail to the promological characteristics of the present variety of peach tree, its characteristics are set forth as observed under the ecological conditions prevailing at the applicant's orchard designated above. The major color plate identifications are by reference to the Nickerson Color Fan of the American Horticultural Council.

*Tree:*

- Size: Large, vigorous.
- Figure: Shape and size determined by pruning practices.
- Productivity: Good.
- Bearing: Regular.
- Trunk: Medium stocky, medium smooth.
- Branches: Lenticels numerous, medium smooth.
- Leaves:
  - Size: Medium to large.
  - Length: 15.25 cm.
  - Width: 3.75 cm.
  - Shape: Lanceolate, tip acuminate.
  - Color: Moderate olive green (2.5GY 4/3) to moderate yellow green (2.5GY 5/5).
  - Marginal Form: Crenate.
  - Glandular characteristics: Reniform, numerous.
  - Petiole: Length—approximately 1 cm. Thickness—approximately .3 cm.
  - Stipules: Usually two and opposed.

*Flower buds:*

- Size: Generally large.
- Shape: Plump.
- Surface: Pubescent.

*Flowers:*

- Dates of bloom: Latter part of March. Same as Preuss Suncrest and Fay Elberta.
- Size: Large.
- Color: Pale to moderate pink (2.5R 9/3–5R 8/5) with some darkening to strong pink (2.5R 7/8).
- Fertile: Self.

*Fruit:*

- Maturity: Third quarter of July, six days before Preuss Suncrest and Merrill 49er, and about sixteen days earlier than the Fay Elberta (unpatented).
- Size: Large under normal conditions, care and thinning.
  - Uniformity: Consistent.
  - Axial diameter: 6.5 cm.
  - Diameter transverse in suture plane: 7 cm.
  - Diameter transverse at right angles to suture plane: 6.75 cm.
- Form:
  - Uniformity: Globose but prominently indented at stem end and somewhat depressed at pistil point.
  - Symmetrical or asymmetric: Symmetrical.
  - Suture: Well filled, shallow. Length—From stem to pistil point.
  - Ventral surface: Rounded, lips equal.
  - Stem cavity: Pronounced.
  - Base: Flat.
  - Apex: Depressed.

Pistil point: Minute.
Stem: Length—Short. Caliper—Stubby.
Skin:
Thickness: Thin.
Texture: Smooth.
Tendency to crack: None.
Color: Yellow (2.5Y 8/12 to 2.5Y 9/9) overlayed with moderate red (2.5R 4/10) to strong red (5R 4/12).
Pubesence: Scant.
Flesh:
Color: Brilliant yellow (2.5Y 9/9 to 5Y 9/9) with somewhat more red streaking than Preuss Suncrest.
Surface of pit cavity: Deep grooved.
Color of pit well: Brilliant yellow (2.5Y 9/9 to 5Y 9/9) with bottoms of grooves brilliant yellow to moderate red (2.5R 4/10).
Amygdalin: None observed.
Juice: Abundant.
Flavor: Sweet, subacid.
Aroma: Distinct.
Texture: Fine.
Fibers: Fine.
Ripening: Even.
Eating quality: Excellent.
Stone: Free.
Fibers: Short.
Size: 4 cm. by 2.5 cm. by 2 cm.
Form: Obovate, tip acuminate, asymmetrical, one side bladed with bladed edge concave adjacent to the tip.
Base: Straight.

Sides: Unequal.
Ridges: Prominent.
Color: Strong yellowish brown (10YR 5/6) to strong red (2.5R 5/12).
Splitting tendency: None observed.
Use: Fresh, frozen, canned and dried.
Keeping quality: Excellent.
Shipping quality: Excellent.
Resistance to disease: None observed.

It is to be understood that the peach tree and its fruit described above may vary in response to variations in climate, soil, and cultural conditions. However, when grown with proper farming techniques under the ecological conditions prevailing in the eastern part of the county of Fresno of the State of California, its characteristics are as described above.

What is claimed is:

1. A new and distinct variety of peach tree substantially as illustrated and described which is generally similar to the Preuss Suncrest (U.S. Plant Pat. No. 2,797) in vigorous growth, and in regular heavy bearing of yellow-fleshed freestone fruit which are somewhat more spherical, have skin which has more yellow and somewhat less red, but of a brighter and lighter shade, than the Preuss Suncrest and which ripens approximately six days earlier than the Preuss Suncrest and the Merrill 49er (unpatented) and about sixteen days earlier than the Fay Elberta (unpatented).

No references cited.

ROBERT E. BAGWILL, Primary Examiner